United States Patent
Vicente Matilla et al.

(10) Patent No.: US 10,934,250 B2
(45) Date of Patent: Mar. 2, 2021

(54) PROCESS FOR THE PREPARATION OF A CHELATING AGENT

(71) Applicant: TRADE CORPORATION INTERNATIONAL, S.A. UNIPERSONAL, Madrid (ES)

(72) Inventors: Rebeca Vicente Matilla, Sanchidrián (ES); José María Blasco Barrio, Sanchidrián (ES)

(73) Assignee: TRADE CORPORATION INTERNATIONAL, S.A. UNIPERSONAL, Madrid (ES)

( * ) Notice: Subject to any disclaimer, the term of this patent is extended or adjusted under 35 U.S.C. 154(b) by 262 days.

(21) Appl. No.: 16/062,085

(22) PCT Filed: Dec. 21, 2016

(86) PCT No.: PCT/EP2016/082067
§ 371 (c)(1),
(2) Date: Jun. 13, 2018

(87) PCT Pub. No.: WO2017/108884
PCT Pub. Date: Jun. 29, 2017

(65) Prior Publication Data
US 2019/0002395 A1  Jan. 3, 2019

(30) Foreign Application Priority Data
Dec. 22, 2015 (EP) .................... 15382657

(51) Int. Cl.
*C07C 227/12* (2006.01)
*C05D 9/02* (2006.01)
(Continued)

(52) U.S. Cl.
CPC ............ *C07C 227/12* (2013.01); *A01N 37/44* (2013.01); *C05D 9/02* (2013.01); *C07C 227/14* (2013.01); *C07C 229/36* (2013.01); *C07C 229/76* (2013.01)

(58) Field of Classification Search
CPC ...... A01N 37/44; A01N 37/30; A61K 47/547; C07C 227/12
See application file for complete search history.

(56) References Cited

U.S. PATENT DOCUMENTS 2,921,847 A * 1/1960 Knell .................. C05D 9/02
71/1
3,567,752 A 3/1971 Israily
(Continued)

FOREIGN PATENT DOCUMENTS

CH         561226 A5   4/1975
GB         1418888 A  12/1975
RU         2278868 C1   6/2006

OTHER PUBLICATIONS

Kari Ylivainio, "Environmentally Benign Fe Chelates in Plant Nutrition", University of Helsinki, PhD Dissertation (2009) (Year: 2009).*
Huntsman, "Ethyleneamines: A Global Profile of Products and Services", accessed from www.huntsman.com <https://files.mutualcdn.com/alfa-chemicals/brochures/product-ranges/Hunt-94-ethyleneamines-brochure.pdf> (2007) (Year: 2007).*
Dow, "Ethyleneamines", accessed from www.dow.com <https://www.dow.com/content/dam/dcc/documents/en-us/catalog-selguide/108/108-01347-01-dow-ethyleneamine-product-selection-guide.pdf?iframe=true> (2009) (Year: 2009).*
Alvarez-Fernandez, et al: "Evaluation of synthetic iron (III)-chelates (EDDHA/Fe3+, EDDHMA/Fe3+ and the novel EDDHSA/Fe3+) to correct iron chlorosis," European Journal of Agronomy 2005; vol. 22, pp. 119-130.
(Continued)

*Primary Examiner* — Jennifer A Smith
*Assistant Examiner* — Amanda Garley
(74) *Attorney, Agent, or Firm* — Squire Patton Boggs (US) LLP

(57) ABSTRACT

It is provided a compound of formula (I'); wherein $R^5$ is selected from the group consisting of —H, —OM, —COOM, —NH$_2$, —SO$_3$M, (C$_1$-C$_4$)alkyl, and halogen; and A is a radical having at least 3 C atoms selected from the group consisting of: i) a radical of formula (i) wherein $R^7$ is selected from the group consisting of —OM, and —COOM, and n is 0, 1 or 2; and ii) a radical of formula (ii) or of formula (iii) wherein $R^8$ is selected from the group consisting of —H, (C$_1$-C$_4$)alkyl; and wherein M is independently selected from the group consisting of H, an alkaly metal, and NH$_4^+$. It is also provided a process for the preparation thereof, a composition comprising it, and its use for correcting deficiencies of metals in plants.

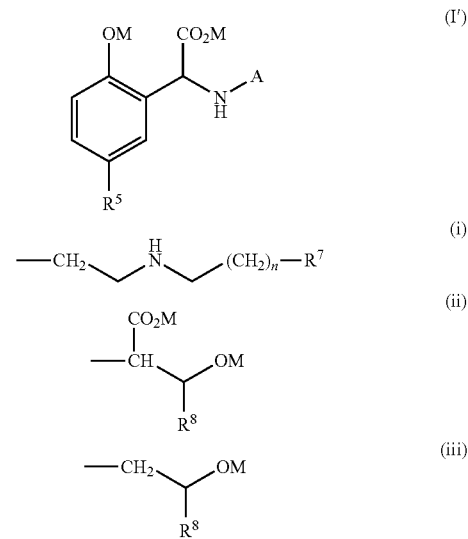

11 Claims, No Drawings

(51) Int. Cl.
  *C07C 229/36*  (2006.01)
  *C07C 227/14*  (2006.01)
  *A01N 37/44*  (2006.01)
  *C07C 229/76*  (2006.01)

(56) References Cited

U.S. PATENT DOCUMENTS

| 3,825,592 A | 7/1974 | McCrary et al. |
| 2007/0261453 A1* | 11/2007 | McKenzie ............... C05D 9/02 71/27 |

OTHER PUBLICATIONS

International Search Report and Written Opinion dated Apr. 20, 2017 for PCT Application No. PCT/EP2016/082067, 13 pages.
Alexandrovna: "Obtaining and Application of Biologically available Iron Compounds Stabilized with Humic Substances", Thesis, Specialty Mar. 2, 2008'Ecology (in chemistry) Dissertation for obtaining a scientific degree; Moscow State University 2014, 164 pages.

* cited by examiner

PROCESS FOR THE PREPARATION OF A CHELATING AGENT

This application is a national stage entry of PCT/EP2016/082067, filed on Dec. 21, 2016, which claims the benefit of European patent application 15382657.3, filed Dec. 22, 2015; the contents of both of which are incorporated herein by reference in their entireties.

The present invention relates to novel chelating agents which are useful over a wide pH range and, particularly, in alkaline or neutral environments, and to metal chelates thereof, particularly iron chelates. The invention also relates to a process for the preparation of chelating agents and to metal chelates thereof, more particularly for the preparation of phenolic amino acids and derivatives thereof useful as chelating agents and to metal chelates thereof.

BACKGROUND ART

Alpha-imino-o-hydroxyphenylacetic acids and derivatives thereof of the following general formula:

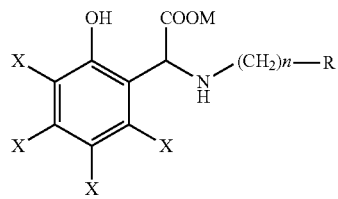

wherein X is H, —COOH, —NO$_2$, —Cl, —CH$_3$, —NH$_2$ o SO$_3$H; R is —COOH, —CH$_2$OH, or —SH; n is an integer from 1 to 10, preferably 1 or 2; and M is a H or a cation of a metal, preferably an alkali metal, or of a basic organic compound such as an amine or aminoalcohol, are known to be compounds capable of complexing with metal cations, particularly iron cations, to form stable chelates suitable for correcting deficiencies of these metals in plants grown on both acid and alkaline soils.

Several processes for the preparation of the mentioned or related compounds has been disclosed such in U.S. Pat. No. 3,567,752, GB1418888, and U.S. Pat. No. 3,825,592. Nevertheless, these documents disclose processes wherein water is and/or other solvents are used as a solvent, and some of them proceed by using hazardous reactants. Yields achieved in these processes are not as good as desired. Particularly, in U.S. Pat. No. 3,567,752 [2-(o-hydroxyphenyl)]-2-hydroxyethyl-glycine is obtained in several steps, including the use of ethylene dichloride as a solvent and of hydrogen cyanide as one of the reactants.

Despite the teaching of these prior art documents, the provision of improved chelating compound is still a matter of great interest in industry. It is also of interest the provision of an improved process for the preparation of alpha-imino-o-hydroxyphenylacetic acids and derivatives thereof in higher yields and regioselectivities.

SUMMARY OF THE INVENTION

The present inventors have found new chelating compounds which are useful to make metal cations, particularly iron, available to plants. Additionally, the free chelating agent of the invention can also solubilize and make available to plants traces of metals, particularly of iron, already present in soils, particularly in acid and alkaline soils.

Accordingly, a first aspect of the invention refers to a chelating compound of formula (I');

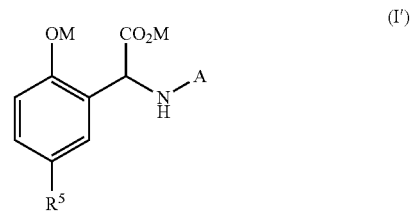

wherein $R^5$ is selected from the group consisting of —H, —OM, —COOM, —NH$_2$, —SO$_3$M, (C$_1$-C$_4$)alkyl, and halogen, such as F or Cl; and A is a radical having at least 3 C atoms selected from the group consisting of:
i) a radical of formula (i)

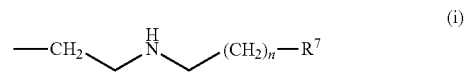

wherein $R^7$ is selected from the group consisting of —OM, and —COOM, and n is 0, 1 or 2; and wherein M is independently selected from the group consisting of H, an alkaly metal such as Na$^+$ or K$^+$, and NH$_4^+$;

ii) a radical of formula (ii)

wherein $R^8$ is selected from the group consisting of —H, (C$_1$-C$_4$)alkyl; and wherein M is independently selected from the group consisting of H, an alkaly metal such as Na$^+$ or K$^+$, and NH$_4^+$; or iii) a radical of formula (iii)

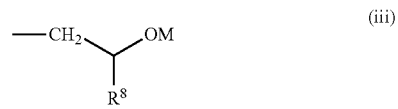

wherein $R^8$ is (C$_1$-C$_4$)alkyl; and wherein M is independently selected from the group consisting of H, an alkaly metal such as Na$^+$ or K$^+$, and NH$_4^+$.

The compounds of the invention are capable of complexing with metal cations, especially iron cations, to form stable chelates which are suitable for correcting deficiencies of these metals in plants, particularly in plants grown on both acid and alkaline soils. Thus, metal chelates, particularly iron chelates, of compounds of formula (I') as defined above also form part of the invention.

Accordingly, another aspect of the invention refers to a metal chelate, particularly an iron chelate, of any one of the chelating compounds as defined above.

Surprisingly, compared with known similar chelated compounds, the chelated compounds of the invention have a higher stability. Consequently, the chelate and chelating compounds of the invention are more effective in making iron available to plants. This is also related with the more effectiveness of the chelating agent of the invention in solubilizing and making available to plants traces of iron already present in soils, particularly in acid and alkaline soils. A further aspect of the invention relates to a process for the preparation of any one of the metal chelates, particularly of the iron chelates, as defined above comprising adding a salt of the metal to the chelating compounds as defined above.

Still another aspect of the invention relates to a composition either comprising the chelating compound of formula (I') depicted above or a metal chelate thereof, particularly an iron chelate thereof, together with agriculturally acceptable carriers.

Another aspect of the invention relates to the use of the compound of formula (I') or a metal chelate thereof for correcting deficiencies of metals, particularly of iron, in plants by making metal cations available to plants, particularly in plants grown on both acid and alkaline soils.

Another aspect of the invention relates to a process for the preparation of a compound of formula (I') as defined above, the process comprising
reacting a compound of formula (II')

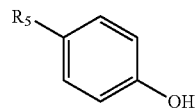
(II')

wherein $R^5$ is H or $CH_3$, with
a-i) a compound of the following formula

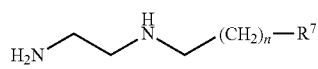

wherein $R^7$ is selected from the group consisting of —OM, and —COOM, and n is 0, 1 or 2, and M is independently selected from the group consisting of H, an alkaly metal, and $NH_4^+$; or
a-ii) a compound of the following formula

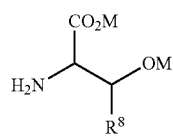

wherein $R^8$ is selected from the group consisting of —H, $(C_1\text{-}C_4)$alkyl, and M is independently selected from the group consisting of H, an alkaly metal, and $NH_4^+$; or
a-iii) with a compound of the following formula

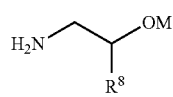

wherein $R^8$ is selected from the group consisting of —H, $(C_1\text{-}C_4)$alkyl, M is independently selected from the group consisting of H, an alkaly metal, and $NH_4^+$; and b) with glyoxylic acid or a salt thereof in the presence of a base, without the addition of an organic solvent, and in the presence of an amount of water from 1 to 13.3 mol for each mol of glyoxylic acid.

Advantageously, the process of the invention overcomes or minimizes the drawbacks of the known processes to obtain this kind of compounds abovementioned (derived from the use of water and/or other solvents as a solvent, or from the use of hazardous reactants). Also advantageously, the new process allows obtaining the mentioned compounds with high yields and regioselectivities, while using reaction conditions easy to scale-up to an industrial level, avoiding the use of harmful reactants, and avoiding some workup steps, thus reducing costs.

The process of the invention is also applicable to the preparation of other α-imino-o-hydroxyphenylacetic acids and derivatives thereof. Accordingly, also forms part of the invention a process for the preparation of a compound of formula (I)

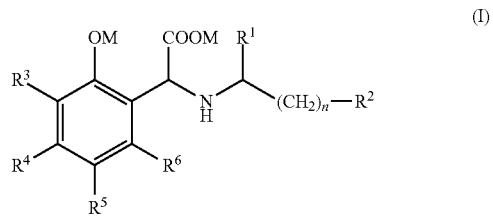
(I)

wherein $R^1$ is selected from the group consisting of H, —OM, —$CH_3$, —COOM, —$CH_2OH$, —$CH(CH_3)(OH)$, and —$NH_2$;

$R^2$ is selected from the group consisting of —H, —OM, —COOM, —$NH_2$, —$CH_3CH(NH_2)(CH_2)_3OH$, —$NH_2(CH_2)_mCOOM$, —$CONH_2$, —$NHC(NH_2)_2$, —SH, —$SCH_3$, —$CH(CH_3)_2$, —$CH(CH_3)(OH)$, —$CH(CH_3)(CHCH_2CH_3)$, -PhOH, -Ph,

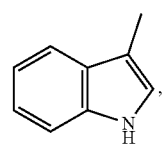

and
—$NH_2(CH_2)_mOM$, wherein m is 1 or 2;
$R^3$, $R^4$, $R^5$, and $R^6$ are independently selected from the group consisting of —H, —OM, —COOM, —$NH_2$, —$SO_3M$, $(C_1\text{-}C_4)$alkyl, and halogen, particularly Cl or F;
wherein M is independently selected from the group consisting of H, an alkaly metal, such as $Na^+$ and $K^+$, and $NH_4^+$, and n is 0 to 1,
the process comprising reacting a compound of formula (II)

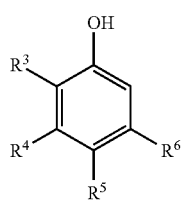
(II)

wherein $R^3$, $R^4$, $R^5$, and $R^6$ are as defined above, with a compound of formula (III)

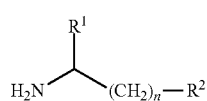
(III)

wherein $R^1$, $R^2$ and n are as defined above, and glyoxylic acid or a salt thereof in the presence of a base, without the addition of an organic solvent, and in the presence of an amount of water from 1 to 13.3 mol for each mol of glyoxylic acid.

DETAILED DESCRIPTION OF THE INVENTION

The term "alkyl" refers to a saturated straight or branched hydrocarbon chain which contains the number of carbon atoms specified in the description or claims. Thus, the term "$(C_1-C_4)$alkyl" refers to a saturated straight, or branched hydrocarbon chain containing from 1 to 4 carbon atoms. Examples include the group methyl, ethyl, propyl, isopropyl, butyl, isobutyl, sec-butyl, and tert-butyl.

According to the International Union of Pure and Applied Chemistry (IUPAC), chelation involves the formation or presence of two or more separate coordinate bonds between a polydentate (multiple bonded) ligand (such as the chelating compounds disclosed herein above and below) and a single central metal atom. The term "metal chelate", as used herein, means a coordination compound in which a metal atom or ion is bound to a chelating agent as defined above and below at two or more points on the ligand, so as to form a heterocyclic ring containing a metal atom.

The term "phenolic compound", as used herein, refers to a compound represented by the formula (II)

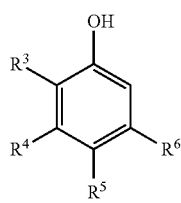
(II)

wherein $R^3$, $R^4$, $R^5$, and $R^6$ are as defined above. Particularly, $R^3$, $R^4$, $R^6$ are H, and $R^5$ is H or $CH_3$ As mentioned above, a first aspect of the invention relates to a chelating compound of formula (I');

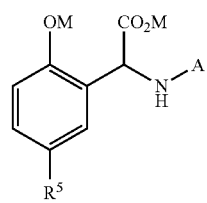
(I')

wherein $R^5$, M and A are as defined above.

In a particular embodiment, the compound of formula (I') is:

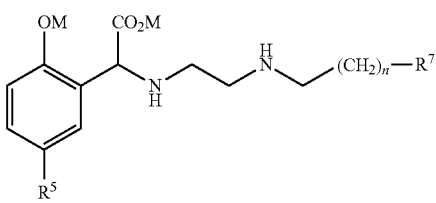

wherein $R^7$ is selected from the group consisting of —OM, and —COOM, and n is 0, 1 or 2; and wherein M is independently selected from the group consisting of H, an alkaly metal, and $NH_4$.

In another particular embodiment, the compound of formula (I') is:

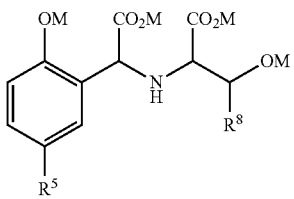

wherein $R^8$ is selected from the group consisting of —H, $(C_1-C_4)$alkyl; and wherein M is independently selected from the group consisting of H, an alkaly metal, and $NH_4^+$.

In another particular embodiment, the compound of formula (I') is:

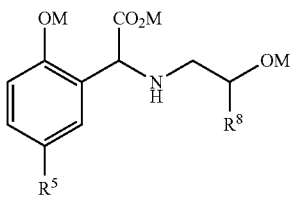

wherein $R^8$ is $(C_1-C_4)$alkyl; and wherein M is independently selected from the group consisting of H, an alkaly metal, and $NH_4^+$.

In another particular embodiment, the compound of formula (I') is selected from the group consisting of:

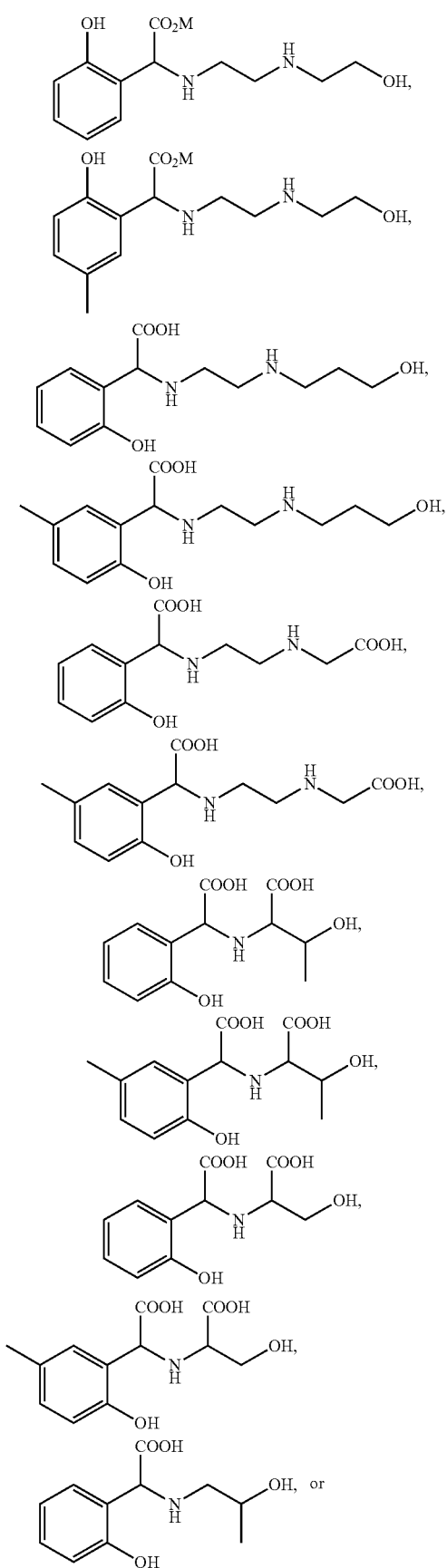

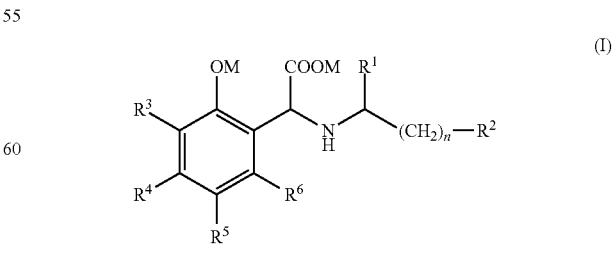

wherein the hydroxyl groups (—OH) can be in the form of —OM, wherein M is independently selected from the group consisting of H, an alkaly metal, and $NH_4^+$. Particularly, M is H. It is also part of the invention a metal chelate of the mentioned compound. Particularly, the metal chelate is an iron chelate.

The compounds of the invention, that is, the compound of formula (I'), particularly the compounds listed above, are capable of complexing with metal cations, especially iron cations, to form stable chelates which are suitable for correcting deficiencies of these metals in plants, particularly in plants grown on both acid and alkaline soils. The stability of the chelated compounds of the invention is higher than the one of already known chelated compounds.

Metal chelates of the chelating compounds defined above can be prepared by adding a salt of the metal to the compounds as defined above. Particularly, the preparation of the ferric chelate can be made by adding a ferric salt such as iron sulfate, iron nitrate or iron trichloride over the aqueous solution mentioned above, and adjusting the pH at 8-9 with a base such as KOH, NaOH, $K_2CO_3$, and $NH_3$. The ferric chelate is isolated by removing water by distillation under reduced pressure.

The amount of metal cation to be added to the chelating compound is from 0.5 to 3 mol with respect to the chelating compound. Particularly, the metal cation is $Fe^{+2}$ or $Fe^{+3}$.

As mentioned above, it is also part of the invention a composition either comprising the chelating compound of formula (I') defined above, particularly the specific compounds depicted above, or a metal chelate thereof, particularly an iron chelate thereof, together with agriculturally acceptable carriers.

Suitable agricultural carriers useful in preparing agricultural compositions of the present invention are well known to those skilled in the art. For example, liquid carriers that can be employed include water. Water is generally the carrier of choice for the dilution of concentrates.

Also as mentioned above, the inventors has found an advantageous process for the preparation of a compound of formula (I)

as defined above, the process comprising reacting a compound of formula (II)

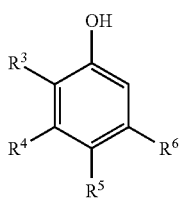
(II)

as defined above, with a compound of formula (III)

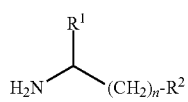
(III)

as defined above, and glyoxylic acid or a salt thereof in the presence of a base, without the addition of an organic solvent, and in the presence of an amount of water from 1 to 13.3 g/g of glyoxylic acid.

This process allows obtaining the final compound with the amino acid substituent at the ortho position with respect to the —OM, particularly —OH, group with yields and selectivities higher than by the processes known in the art, the formation of the para isomer being minimized.

Particularly, the process of the invention comprises reacting a phenolic compound, particularly phenol or a phenolic compound as defined above substituted in para position, with a compound of formula (III) as defined above, particularly an amino acid or an amino alcohol. The reaction takes place in the presence of a base such as KOH, NaOH, $K_2CO_3$, and $NH_3$. Finally, glyoxylic acid or a salt thereof such as sodium glyoxylate is added by keeping the reaction mixture at a temperature from 50° C. to 100° C. More particularly, from 3 to 30 mol of the phenolic compound, from 0.5 to 2 mol of the compound of formula (III) as defined above, from 0.5 to 2 mol of base, and from 0.5 to 2 mol of the glyoxylic acid or a salt thereof are used. Even more particularly, 10 mol of the phenolic compound, 1 mol of the compound of formula (III) as defined above, 1 mol of base, and 1 mol of the glyoxylic acid or a salt thereof are used.

The same phenolic compound used as reactant is used as a solvent, namely no other solvent is added to the reaction mixture, apart from water contained in the solutions of base or of glyoxylic acid used in the reaction. This has the advantage of avoiding some workup steps, such as of precipitation and purification of the final product. Additionally, higher yields and regioselectivities are obtained. Once the reaction finished, particularly after 2-7 hours of reaction, water can be added to the reaction crude to obtain an aqueous solution of the final compound.

In a particular embodiment of the process of the invention $R^1$ is selected from the group consisting of H, —OM, —CH$_3$, —COOM, —CH$_2$OH, —CH(CH$_3$)(OH), and NH$_2$; $R^2$ is selected from the group consisting of —H, —OM, —COOM, —NH$_2$, —CH$_3$CH(NH$_2$)(CH$_2$)$_3$OH, —NH$_2$(CH$_2$)$_m$COOM, and —NH$_2$(CH$_2$)$_m$OM wherein m is 1 or 2; $R^3$, $R^4$, and $R^6$ are H; and $R^5$ is independently selected from the group consisting of —H, —OH, —COOM, —NH$_2$, —SO$_3$M, (C$_1$-C$_4$)alkyl; wherein M is independently selected from the group consisting of H, an alkaly metal, such as Na$^+$ and K$^+$, and NH$_4$$^+$, and n is 0 or 1.

In another particular embodiment of the process of the invention $R^1$ is selected from the group consisting of H, —OM, —CH$_3$, —COOM, —CH$_2$OH, —CH(CH$_3$)(OH), and —NH$_2$; $R^2$ is selected from the group consisting of —H, —OM, —COOM, —NH$_2$, —CH$_3$CH(NH$_2$)(CH$_2$)$_3$OH, —NH$_2$(CH$_2$)$_m$COOM, and —NH$_2$(CH$_2$)$_m$OM wherein m is 1 or 2; $R^3$, $R^4$, and $R^6$ are H; and $R^5$ is independently selected from the group consisting of —H, —OH, —COOM, —NH$_2$, —SO$_3$M, (C$_1$-C$_4$)alkyl; wherein M is independently selected from the group consisting of H, an alkaly metal, such as Na$^+$ and K$^+$, and NH$_4$$^+$, and n is 0 or 1.

In another particular embodiment of the process of the invention, $R^1$ is H; $R^2$ is —OH, —COOM, —NH$_2$, —NH$_2$(CH$_2$)$_m$COOM, and —NH$_2$(CH$_2$)$_m$OM; wherein $R^3$, $R^4$, and $R^6$ are H, and $R^5$ is selected from the group consisting of H, —CH$_3$, and —SO$_3$H; wherein M is independently selected from the group consisting of H, an alkaly metal, such as Na$^+$ and K$^+$, and NH$_4$$^+$; m is 1 or 2; and n is 0 or 1, provided that if n is 0, $R^2$ is —COOM, and if n is 1, $R^2$ is —NH$_2$, —NH$_2$(CH$_2$)$_m$COOM, or —NH$_2$(CH$_2$)$_m$OM, wherein M is independently selected from the group consisting of H, an alkaly metal, such as Na$^+$ and K$^+$, and NH$_4$$^+$.

In another particular embodiment of the process of the invention, a compound of formula (IV):

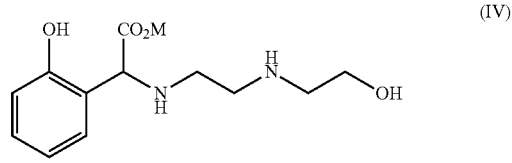
(IV)

or formula (V):

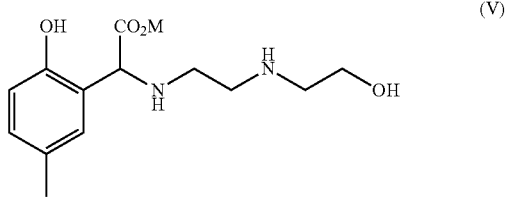
(V)

wherein M is selected from the group consisting of H and an alkali metal such as Na+ and K+, and particularly, M is H, are prepared; wherein the process comprises reacting a compound of formula (II')

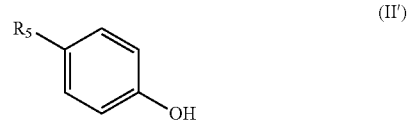
(II')

wherein $R^5$ is H or CH$_3$, with aminoethylethanolamine, and glyoxylic acid or a salt thereof in the presence of a base, without the addition of an organic solvent, and in the presence of an amount of water from 1 to 13.3 mol for each mol of glyoxylic acid.

In another particular embodiment of the process of the invention, a compound of formula (I')

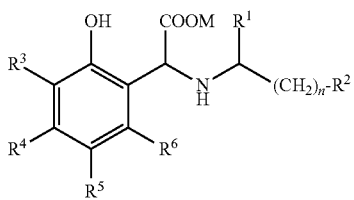

is prepared, wherein the compound of formula (II) is

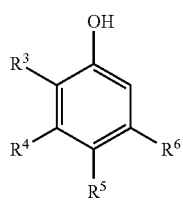

wherein $R^1$, $R^2$, $R^3$, $R^4$, $R^5$, $R^6$, n, m, and M are as defined above.

In another particular embodiment of the process of the invention, a compound of formula (I') as defined above wherein $R^3$, $R^4$, and $R^6$ are H, and $R^5$ is H, —$CH_3$, or —$SO_3H$, is prepared, the process comprising reacting a compound of formula (II')

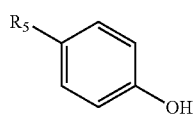

wherein $R^5$ is as defined above,
with a compound of formula (III)

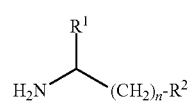

wherein $R^1$ is H, $R^2$ is —OH, —COOM, —$NH_2$, —$NH_2(CH_2)_m$COOM, and —$NH_2(CH_2)_m$OM, wherein M is independently selected from the group consisting of H, an alkaly metal such as $Na^+$ and $K^+$, and $NH_4^+$, m is 1 or 2; and n is 0 or 1; provided that if n is 0, $R^2$ is —COOM, and if n is 1, $R^2$ is —$NH_2$, —$NH_2(CH_2)_m$COOM, and —$NH_2(CH_2)_m$OM;
and glyoxylic acid or a salt thereof in the presence of a base, without the addition of an organic solvent, and in the presence of an amount of water from 1 to 13.3 mol for each mol of glyoxylic acid.

The final compound can be isolated by extraction with an organic solvent such as chloroform and subsequent removal of the solvent by distillation under reduced pressure. Alternatively, the aqueous solution abovementioned containing the compound of interest can be used directly for the chelation of iron.

The obtained compounds can be quantified by potentiometric titration of the amino groups, by measuring the red-violet compound obtained after the addition of a ferric salt at pH 3-7 by HPLC and spectrophotometry.

Compounds of formula (II) and of formula (III) defined above are either commercially available or can be prepared from commercially available compounds by conventional processes known by any expert in the art.

Throughout the description and claims the word "comprise" and variations of the word, are not intended to exclude other technical features, additives, components, or steps. Furthermore, the word "comprise" encompasses the case of "consisting of".

The following examples are provided by way of illustration, and they are not intended to be limiting of the present invention. Furthermore, the present invention covers all possible combinations of particular and preferred embodiments described herein.

EXAMPLES

Example 1. Preparation of monoethanolamine-N-(2-hydroxyphenylacetic acid (MEAHA)

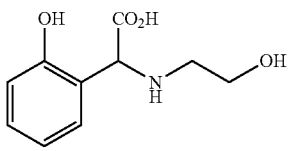 [SMILES: O=C(O)C(NCCO)c1ccccc1O]

To 940 g (10 mol) of phenol at 40° C., 61 g (1 mol) of monoethanolamine was slowly added without leaving the temperature to raise over 45° C. Once the addition was finished, the reaction mixture was allowed to cool down and 80 g (1 mol) of 50% w/w sodium hydroxide aqueous solution was added. After cooling the reaction crude to 35° C., 148 g (1 mol) of 50% w/w glyoxylic acid aqueous solution was slowly and continuously added, keeping the temperature under 40° C. during all the reaction. Then, the mixture was allowed to react for 2-4 hours at 70-75 C. Finally, 90 g (5 mol) of water were added and the aqueous phase was extracted twice with 1120 g (10 mol) of chlorobenzene. The aqueous phase contained the chelating agent MEAHA. Chelation of Fe-MEAHA was subsequently made directly over the obtained aqueous solution.

For the chelation, to the aqueous solution obtained above containing the chelating agent MEAHA, 162.3 g (1 mol) of $FeCl_3$ and 240-320 g (3-4 mol) of 50% w/w sodium hydroxide aqueous solution until obtaining a pH of 8-9 were added.

Finally, after removing water by distillation under reduced pressure, the iron chelate in form of dark brown powder/microgranules was obtained. The iron content of the product varied from 8-9 wt. %.

Example 2. Preparation of monoethanolamine-N-(2-hydroxy-5-methyl-phenylacetic acid (CREMEAHA)

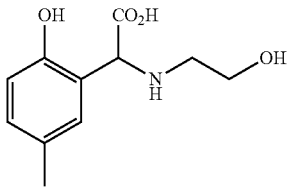 [SMILES: Cc1ccc(O)c(C(NCCO)C(=O)O)c1]

To 1080 g (10 mol) of p-cresol at 40° C., 61 g (1 mol) of monoethanolamine was slowly added without leaving the temperature to raise over 45° C. Once the addition was finished, the reaction mixture was allowed to cool down and 80 g (1 mol) of 50% w/w sodium hydroxide aqueous solution was added. After cooling the reaction crude to 35° C., 148 g (1 mol) of 50% w/w glyoxylic acid aqueous solution was slowly and continuously added, keeping the temperature under 40° C. during all the reaction. Then, the mixture was allowed to react for 2-4 hours at 70-75° C. Finally, 90 g (5 mol) parts of water were added and the aqueous phase was extracted twice with 1120 g (10 mol) of chlorobenzene. The aqueous phase contained the chelating agent CREMEAHA. Chelation of Fe-CREMEAHA was subsequently made directly over the obtained aqueous solution.

For the chelation, to the aqueous solution obtained above containing the chelating agent CREMEAHA, 162.3 g (1 mol) of FeCl$_3$ and 240-320 g (3-4 mol) of 50% w/w sodium hydroxide aqueous solution until obtaining a pH of 8-9 were added.

Finally, after removing water by distillation under reduced pressure, the iron chelate in form of dark brown powder/microgranules was obtained. The iron content of the product varied from 8-9 wt. %.

Example 3. Preparation of aminoethylethanolamine-N-(2-hydroxyphenylacetic acid (NEAHA)

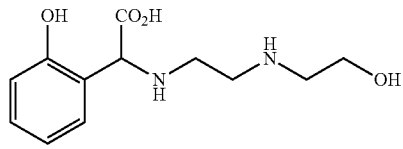 [SMILES: O=C(O)C(NCCNCCO)c1ccccc1O]

To 940 g (10 mol) of phenol at 40° C., 106 g (1 mol) of aminoethylethanolamine was slowly added without leaving the temperature to raise over 45° C. Once the addition was finished, the reaction mixture was allowed to cool down and 80 g (1 mol) of 50% w/w sodium hydroxide aqueous solution was added. After cooling the reaction crude to 35° C., 148 g (1 mol) of 50% w/w glyoxylic acid aqueous solution was slowly and continuously added, keeping the temperature under 40° C. during all the reaction. Then, the mixture was allowed to react for 2-4 hours at 70-75° C. Finally, 90 g (5 mol) parts of water were added and the aqueous phase was extracted twice with 1120 g (10 mol) of chlorobenzene. The aqueous phase contained the chelating agent NEAHA. Chelation of Fe-NEAHA was subsequently made directly over the obtained aqueous solution.

For the chelation, to the aqueous solution obtained above containing the chelating agent NEAHA, 162.3 g (1 mol) of FeCl$_3$ and 240-320 g (3-4 mol) of 50% w/w sodium hydroxide aqueous solution until obtaining a pH of 8-9 were added.

Finally, after removing water by distillation under reduced pressure, the iron chelate in form of dark brown powder/microgranules was obtained. The iron content of the product varied from 7-8 wt. %.

Example 4. Preparation of aminoethylethanolamine-N-(2-hydroxy-5-methyl-phenylacetic acid (CRENEAHA)

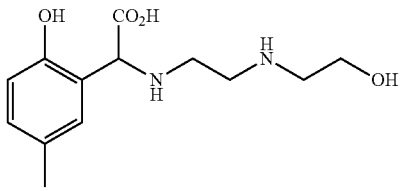 [SMILES: Cc1ccc(O)c(C(NCCNCCO)C(=O)O)c1]

To 1180 g (10 mol) of p-cresol at 40° C., 106 g (1 mol) of aminoethylethanolamine was slowly added without leaving the temperature to raise over 45° C. Once the addition was finished, the reaction mixture was allowed to cool down and 80 g (1 mol) of 50% w/w sodium hydroxide aqueous solution was added. After cooling the reaction crude to 35° C., 148 g (1 mol) of 50% w/w glyoxylic acid aqueous solution was slowly and continuously added, keeping the temperature under 40° C. during all the reaction. Then, the mixture was allowed to react for 2-4 hours at 70-75° C. Finally, 90 g (5 mol) parts of water were added and the aqueous phase was extracted twice with 1120 g (10 mol of chlorobenzene. The aqueous phase contained the chelating agent CRENEAHA. Chelation of Fe-CRENEAHA was subsequently made directly over the obtained aqueous solution.

For the chelation, to the aqueous solution obtained above containing the chelating agent CRENEAHA, 162.3 g (1 mol) of FeCl$_3$ and 240-320 g (3-4 mol) of 50% w/w sodium hydroxide aqueous solution until obtaining a pH of 8-9 were added.

Finally, after removing water by distillation under reduced pressure, the iron chelate in form of dark brown powder/microgranules was obtained. The iron content of the product varied from 7-8 wt. %.

Example 5. Preparation of Compound of Formula (VI) (GLYHA)

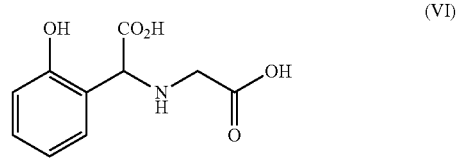 [SMILES: O=C(O)CNC(C(=O)O)c1ccccc1O]

(VI)

To 940 g (10 mol) of phenol at 40° C., 75 g (1 mol) of glycine was slowly added without leaving the temperature to raise over 45° C. Once the addition was finished, the reaction mixture was allowed to cool down and 80 g (1 mol) of 50% w/w sodium hydroxide aqueous solution was added. After cooling the reaction crude to 35° C., 148 g (1 mol) of 50% w/w glyoxylic acid aqueous solution was slowly and continuously added, keeping the temperature under 40° C. during all the reaction. Then, the mixture was allowed to react for 2-4 hours at 70-75° C. Finally, 90 g (5 mol) parts of water were added and the aqueous phase was extracted twice with 1120 g (10 mol of chlorobenzene. The aqueous phase contained the chelating agent GLYHA. Chelation of Fe-GLYHA was subsequently made directly over the obtained aqueous solution.

For the chelation, to the aqueous solution obtained above containing the chelating agent GLYHA, 162.3 g (1 mol) of $FeCl_3$ and 240-320 g (3-4 mol) of 50% w/w sodium hydroxide aqueous solution until obtaining a pH of 8-9 were added.

Finally, after removing water by distillation under reduced pressure, the iron chelate in form of dark brown powder/microgranules was obtained. The iron content of the product varied from 8-9 wt. %.

Example 6. Preparation of Compound of Formula (VII) (CREGLYHA)

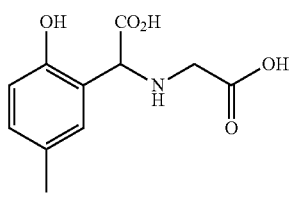

(VII)

To 1180 g (10 mol) of p-cresol at 40° C., 75 g (1 mol) of glycine was slowly added without leaving the temperature to raise over 45° C. Once the addition was finished, the reaction mixture was allowed to cool down and 80 g (1 mol) of 50% w/w sodium hydroxide aqueous solution was added. After cooling the reaction crude to 35° C., 148 g (1 mol) of 50% w/w glyoxylic acid aqueous solution was slowly and continuously added, keeping the temperature under 40° C. during all the reaction. Then, the mixture was allowed to react for 2-4 hours at 70-75° C. Finally, 90 g (5 mol) parts of water were added and the aqueous phase was extracted twice with 1120 g (10 mol of chlorobenzene. The aqueous phase contained the chelating agent CREGLYHA. Chelation of Fe-CREGLYHA was subsequently made directly over the obtained aqueous solution.

For the chelation, to the aqueous solution obtained above containing the chelating agent CREGLYHA, 162.3 g (1 mol) of $FeCl_3$ and 240-320 g (3-4 mol) of 50% w/w sodium hydroxide aqueous solution until obtaining a pH of 8-9 were added.

Finally, after removing water by distillation under reduced pressure, the iron chelate in form of dark brown powder/microgranules was obtained. The iron content of the product varied from 8-9 wt. %.

Example 7. Preparation of Compound of Formula (VIII) (ASPHA)

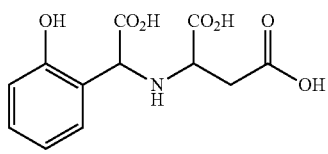

(VIII)

To 940 g (10 mol) of phenol at 40° C., 133 g (1 mol) of aspartic acid was slowly added without leaving the temperature to raise over 45° C. Once the addition was finished, the reaction mixture was allowed to cool down and 80 g (1 mol) of 50% w/w sodium hydroxide aqueous solution was added. After cooling the reaction crude to 35° C., 148 g (1 mol) of 50% w/w glyoxylic acid aqueous solution was slowly and continuously added, keeping the temperature under 40° C. during all the reaction. Then, the mixture was allowed to react for 2-4 hours at 70-75° C. Finally, 90 g (5 mol) parts of water were added and the aqueous phase was extracted twice with 1120 g (10 mol of chlorobenzene. The aqueous phase contained the chelating agent ASPHA. Chelation of Fe-ASPHA was subsequently made directly over the obtained aqueous solution.

For the chelation, to the aqueous solution obtained above containing the chelating agent ASPHA, 162.3 g (1 mol) of $FeCl_3$ and 240-320 g (3-4 mol) of 50% w/w sodium hydroxide aqueous solution until obtaining a pH of 8-9 were added.

Finally, after removing water by distillation under reduced pressure, the iron chelate in form of dark brown powder/microgranules was obtained. The iron content of the product varied from 8-9 wt. %.

Example 8. Preparation of Compound of Formula (IX) (CREASPHA)

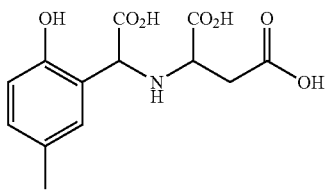

(IX)

To 1180 g (10 mol) of p-cresol at 40° C., 133 g (1 mol) of aspartic acid was slowly added without leaving the temperature to raise over 45° C. Once the addition was finished, the reaction mixture was allowed to cool down and 80 g (1 mol) of 50% w/w sodium hydroxide aqueous solution was added. After cooling the reaction crude to 35° C., 148 g (1 mol) of 50% w/w glyoxylic acid aqueous solution was slowly and continuously added, keeping the temperature under 40° C. during all the reaction. Then, the mixture was allowed to react for 2-4 hours at 70-75° C. Finally, 90 g (5 mol) parts of water were added and the aqueous phase was extracted twice with 1120 g (10 mol of chlorobenzene. The aqueous phase contained the chelating agent CREASPHA. Chelation of Fe-CREASPHA was subsequently made directly over the obtained aqueous solution.

For the chelation, to the aqueous solution obtained above containing the chelating agent CREASPHA, 162.3 g (1 mol) of $FeCl_3$ and 240-320 g (3-4 mol) of 50% w/w sodium hydroxide aqueous solution until obtaining a pH of 8-9 were added.

Finally, after removing water by distillation under reduced pressure, the iron chelate in form of dark brown powder/microgranules was obtained. The iron content of the product varied from 8-9 wt. %.

Example 9. Preparation of (carboxy (2-hydroxyphenyl)methyl) serine (SERHA)

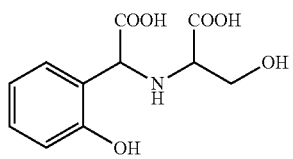 [SMILES: O=C(O)C(CO)NC(C(=O)O)c1ccccc1O]

To 940 g (10 mol) of phenol at 40° C., 105 g (1 mol) of serine was slowly added without leaving the temperature to raise over 45° C. Once the addition was finished, the reaction mixture was allowed to cool down and 80 g (1 mol) of 50% w/w sodium hydroxide aqueous solution was added. After cooling the reaction crude to 35° C., 148 g (1 mol) of 50% w/w glyoxylic acid aqueous solution was slowly and continuously added, keeping the temperature under 40° C. during all the reaction. Then, the mixture was allowed to react for 2-4 hours at 70-75° C. Finally, 90 g (5 mol) parts of water were added and the aqueous phase was extracted twice with 1120 g (10 mol of chlorobenzene. The aqueous phase contained the chelating agent SERHA.

Chelation of Fe-SERHA was subsequently made directly over the obtained aqueous solution. For the chelation, to the aqueous solution obtained above containing the chelating agent SERHA, 162.3 g (1 mol) of $FeCl_3$ and 240-320 g (3-4 mol) of 50% w/w sodium hydroxide aqueous solution until obtaining a pH of 8-9 were added. Finally, after removing water by distillation under reduced pressure, the iron chelate in form of dark brown powder/microgranules was obtained. The iron content of the product varied from 8-9 wt. %.

Example 10. Preparation 2-(2-hydroxyphenyl)-2-((2-hydroxypropyl) amino) acetic acid (AMPHA)

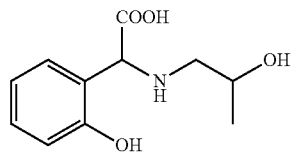 [SMILES: CC(O)CNC(C(=O)O)c1ccccc1O]

To 940 g (10 mol) of phenol at 40° C., 75 g (1 mol) of 1-amino 2-propanol was slowly added without leaving the temperature to raise over 45° C. Once the addition was finished, the reaction mixture was allowed to cool down and 80 g (1 mol) of 50% w/w sodium hydroxide aqueous solution was added. After cooling the reaction crude to 35° C., 148 g (1 mol) of 50% w/w glyoxylic acid aqueous solution was slowly and continuously added, keeping the temperature under 40° C. during all the reaction. Then, the mixture was allowed to react for 2-4 hours at 70-75 C. Finally, 90 g (5 mol) of water were added and the aqueous phase was extracted twice with 1120 g (10 mol) of chlorobenzene. The aqueous phase contained the chelating agent AMPHA. Chelation of Fe-AMPHA was subsequently made directly over the obtained aqueous solution.

For the chelation, to the aqueous solution obtained above containing the chelating agent AMPHA, 162.3 g (1 mol) of $FeCl_3$ and 240-320 g (3-4 mol) of 50% w/w sodium hydroxide aqueous solution until obtaining a pH of 8-9 were added. Finally, after removing water by distillation under reduced pressure, the iron chelate in form of dark brown powder/microgranules was obtained. The iron content of the product varied from 8-9 wt. %.

Example 11. Stability of Chelates

Stability constant of the $Fe^{3+}$ chelate compound of Example 4 (CRENEAHA) were determined spectrophotometrically by titration of a $2.22 \cdot 10^{-4}$ M (12.5 mg/L) and I=0.10M (NaCl) with 0.1 M NaOH from a pH of 2.7 to a pH of 12.0 and measuring the absorbance variation at 480 nm.

Stability constant of the $Fe^{3+}$ chelate compound of Example 2 (CREMEAHA) were determined spectrophotometrically by titration of a $4.49 \cdot 10^{-4}$ M (12.5 mg/L) and I=0.10M (NaCl) with 0.1 M NaOH from a pH of 2.7 to a pH of 12.0 and measuring the absorbance variation at 480 nm.

Stability constants were determined minimizing the difference between calculated absorbance and experimental absorbance by varying the stability constants of $Fe^{3+}$. Every assay was repeated four times. The stability constant value for each compound is not dependent on the concentration of the solution used to carry out the spectrophotometric titration.

Stability constants obtained for the system chelant agent: $Fe^{3+}$ 1:1 are shown in Table 1 below:

TABLE 1

| Especie | | CRENEAHA | CREMEAHA |
|---|---|---|---|
| L + $Fe^{3+}$ –> | FeL | 33.4 | 28.6 |
| L + $H^+$ + $Fe^{3+}$ –> | FeHL | 37.5 | 33.9 |
| L + $OH^-$ + $Fe^{3+}$ –> | FeOHL | 26.9 | 21.2 |

FeHL is the predominant specie at pH <4.0, FeL is the predominant specie at pH from 4 to 6.5, and FeOHL is the predominant specie at pH >6.5.

It can be concluded that the $Fe^{3+}$ chelate obtained in Example 4 (from CRENEAHA compound) has a better stability, particularly at high pH, than the $Fe^{3+}$ chelate obtained in Example 2 (from CREMEAHA). Consequently, the chelate compounds of the invention are more effective in making iron available to plants. This is also related with the more effectiveness of the chelating agent of the invention in solubilizing and making available to plants traces of iron already present in soils, particularly in acid and alkaline soils.

REFERENCES CITED IN THE APPLICATION

1. U.S. Pat. No. 3,567,752
2. GB1418888
3. U.S. Pat. No. 3,825,592

The invention claimed is:
1. A compound of formula (I');

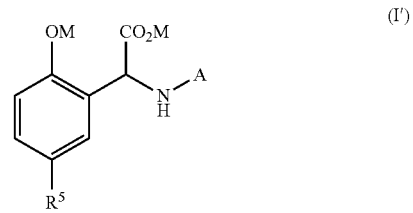

wherein $R^5$ is selected from the group consisting of —H, —OM, —COOM, —NH$_2$, —SO$_3$M, ($C_1$-$C_4$)alkyl, and halogen; and
A is a radical of formula (i)

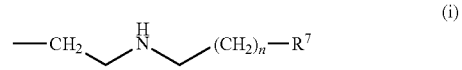

wherein $R^7$ is selected from the group consisting of —OM, and —COOM, and n is 0, 1 or 2; and wherein each M is independently selected from the group consisting of H, an alkali metal, and $NH_4^+$.

2. The compound of claim 1 which is:

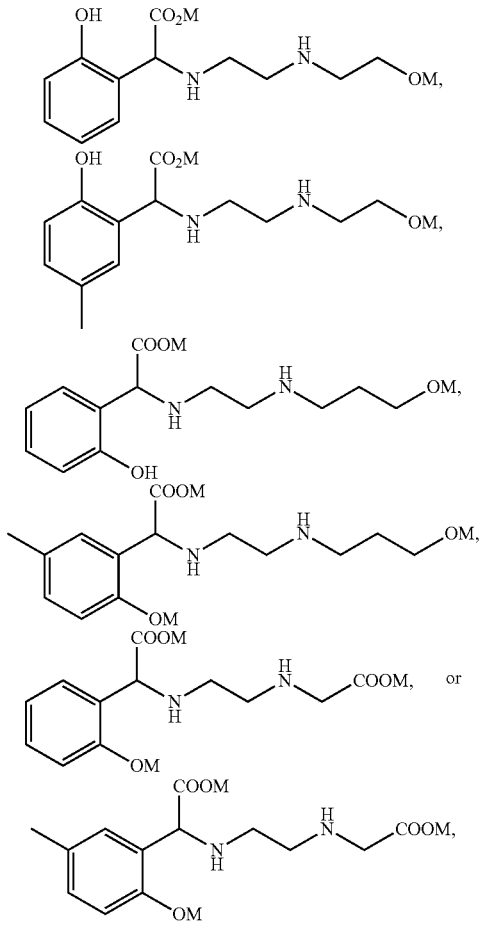

wherein each M is independently selected from the group consisting of H, an alkali metal, and $NH_4^+$.

3. A metal chelate of the compound as defined in claim 2.
4. A metal chelate of the compound as defined in claim 1.
5. The metal chelate of claim 4 which is an iron chelate.
6. A composition comprising the metal chelate of claim 4 together with one or more agriculturally acceptable carriers.
7. A composition comprising the compound of claim 1 together with one or more agriculturally acceptable carriers.
8. A process for the preparation of a compound of formula (I'),

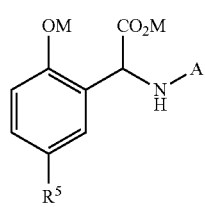

wherein $R^5$ is selected from the group consisting of —H, —OM, —COOM, —$NH_2$, —$SO_3M$, ($C_1$-$C_4$)alkyl, and halogen; and A is a radical of formula (i)

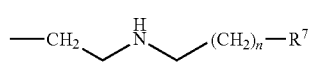

wherein $R^7$ is selected from the group consisting of —OM, and —COOM, and n is 0, 1 or 2; and
wherein each M is independently selected from the group consisting of H, an alkali metal, and $NH_4^+$,
the process comprising
reacting a compound according to the following formula

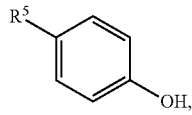

a) with a compound of the following formula

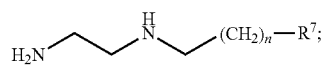

and
b) with glyoxylic acid or a salt thereof in the presence of a base, without the addition of an organic solvent, and in the presence of an amount of water from 1 to 13.3 mol for each mol of glyoxylic acid.

9. The process according to claim 8, the process comprising reacting a compound of formula (II')

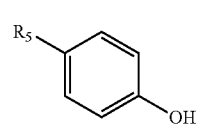

wherein $R^5$ is H or $CH_3$,
a) with a compound of the following formula

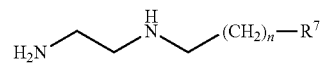

wherein $R^7$ is selected from the group consisting of —OM, and —COOM, and n is 0, 1 or 2, and each M is independently selected from the group consisting of H, an alkali metal, and $NH_4^+$; and
b) with glyoxylic acid or a salt thereof in the presence of a base, without the addition of an organic solvent, and in the presence of an amount of water from 1 to 13.3 mol for each mol of glyoxylic acid.

10. The process of claim 9, further comprising forming a metal chelate by adding a salt of the metal.
11. The process of claim 8, further comprising forming a metal chelate by adding a salt of the metal.

* * * * *